United States Patent
Singh et al.

[11] Patent Number: 5,986,108
[45] Date of Patent: *Nov. 16, 1999

[54] 4-SUBSTITUED-3-[1 OR 2 AMINO ACID RESIDUE]-AZETIDIN-2-ONE DERIVATIVES USEFUL AS CYSTEINE PROTEINASE INHIBITOR

[75] Inventors: Rajeshwar Singh; Nian En Zhou; Deqi Guo, all of Edmonton; Ronald G. Micetich, Sherwood Park, all of Canada

[73] Assignee: Synphar Laboratories, Inc., Edmonton, Canada

[ * ] Notice: This patent is subject to a terminal disclaimer.

[21] Appl. No.: 08/925,459

[22] Filed: Sep. 8, 1997

Related U.S. Application Data

[63] Continuation of application No. 08/415,055, Mar. 31, 1995, abandoned.

[51] Int. Cl.$^6$ .................................................. C07D 205/00
[52] U.S. Cl. .......................... 548/953; 548/920; 514/210; 514/19; 540/200
[58] Field of Search .............................. 540/200; 514/19; 514/210; 548/950, 953

[56] References Cited

FOREIGN PATENT DOCUMENTS 053 816  5/1988  European Pat. Off. .

OTHER PUBLICATIONS

Firestone, Raymond A. et al, "Monocyclic β–Lactam Inhibitors of Human Leukocyte Elastase," *Tetrahedron*, vol. 46, No. 7, pp. 2255–2262, 1990.

2–Azetidinecarboxylic acid, 3–[[[[(4–butyl–2, 3–dioxo–1–piperazinyl) carbonyl] amino] phenylacetyl] amino]–4–oxo–, methyl ester, [2R–[2.alpha., 3.alpha. (R*)]]–, RN 84237–30–9.

Allen Krantz, et al, Peptidyl (Acyloxy)methyl Ketones and the Quiescent Affinity Label Concept: The Departing Group as a Variable Structural Element in the Design of Inactivators of Cysteine Proteinases, *Biochemisty* 1991, 30, 4678–4687.

Dieter Hoppe and Thomas Hilpert, "Enantioselective Total Synthesis of the Fungicide β–Lactam Antibiotic (–)–(2S, 5S)–2(2–Hydroxyethyl) Clavam and its (+)–(2S, 5S)–Epimer", Tetrahedon, vol. 43, No. 11, pp. 2467–2474, 1987.

Toshiyuki Konosu and Sadao Oida, Enantiocontrolled Synthesis of the Antifungal β–Lactam (2R, 5S)–2–(Hydroxymethyl)clavam, Chem. Pharm. Bull. 39(9) pp. 2212–2215, (1991).

J.C. Arnould, P. Boutron, M.J. Pasquet, "Synthesis and Antibacterial Acitviity of C4 Substituted Monobactams", Eur. J. Med Chem. (1992) 27; pp. 131–140.

Hans–Ulrich Demuth"Recent Developments In Inhibiting Cysteine and Serine Proteases", J. Enzyme Inhib. 1990, vol. 3, pp. 249–278.

C.M. Cimarusti et al, "4–Alkylated Monobactams", Tetrahedon, (1983), vol. 39, No. 15, pp. 2577–2589.

*Primary Examiner*—Cecilia Tsang
*Assistant Examiner*—David Lukton
*Attorney, Agent, or Firm*—Nikaido, Marmelstein, Murray & Oram, LLP.

[57] ABSTRACT

Disclosed herein are azetidin-2-one compounds which exhibit excellent cysteine proteinase inhibitory activity. The compounds are 4-substituted-3-{1 or 2 amino acid residue}-azetidin-2-ones of forumula I

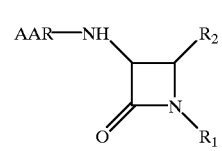

wherein AAR is a 1 or 2 acid residue, and $R_1$ and $R_2$ are as defined herein. The compounds can be used in the treatment of various diseases such as muscular dystrophy, bone resorption disorders, myocardial infarction and cancer metastasis.

21 Claims, No Drawings

4-SUBSTITUED-3-[1 OR 2 AMINO ACID RESIDUE]-AZETIDIN-2-ONE DERIVATIVES USEFUL AS CYSTEINE PROTEINASE INHIBITOR

This application is a continuation of application Ser. No. 08/415,055 filed Mar. 31, 1995, now abandoned.

BACKGROUND OF INVENTION

Cysteine proteinases containing a highly reactive cysteine residue with a free thiol group at the active site have been known as playing important role in certain conditions distinguished by aberrant protein turnover such as: muscular dystrophy (Am. J. Pathol. 1986, 122, 193–198, Am. J. Pathol. 1987, 127, 461–466), bone resorption (Biochem. J. 1991, 279, 167–274), myocardial infarction (J. Am. Coll. Cardiol. 1983, 2, 681–688), cancer metastasis (Cancer Metastasis Rev. 1990, 9, 333–352) and pulmonary emphysema (Am. Rev. Respir. Dis. 1975,111, 579–586). A variety of cysteine proteinases have been shown to be present in mammalian tissue. The most notable of these proteinases are the lysosomal cathepsins (cathepsin B, H, S, and L) and the cytoplasmic $Ca^{2+}$ dependent enzymes, the calpains. These enzymes are, therefore, excellent targets for the development of specific inhibitors as possible therapeutic agents for the conditions such as those noted above.

Cysteine proteinases are inhibited by several types of peptide derived inhibitors such as peptidyl aldehyde (Eur. J. Biochem. 1982, 129, 33–41), chloromethyl ketone (acta. Biol. Med. Ger. 1981, 40, 1503–1511), diazomethyl ketone (Biochemistry 1977, 16, 5857–5861), monofluoromethyl ketone (Biochemical Pharmacology 1992 44, 1201–1207), acyloxy methyl ketone (J. Med. Chem. 1994, 37, 1833–1840), O-acyl hydroxamates (Biochem. Biophy. Research Communications 1988, 155, 1201–1206), methyl sulphenium salts (J.

Biol Chem. 1988, 263, 2768–2772) and epoxy succinyl derivatives (Agric. Biol. Chem. 1978, 42, 523–527) which do not significantly inhibit other classes of proteinases.

These inhibtors, in general, have peptidyl affinity groups and reactive groups towards the thiol of the cysteine residue of cysteine proteinase. Some of the inhibitors are clinically useful. However, their effectiveness in vivo is not as much as expected on the basis of in vitro inhibitory actvity, perhaps due to lower selectivity towards other proteinases and poor pharmacokinetics. Therefore, there exits a continuing need to develop new cysteine proteinase inhibitors with high selectivity and lower toxicity.

Peptidyl-CO—Y
Y = H, $CH_2Cl$, $CHN_2$, $CH_2F$,
$CH_2OCOAr$, NHOCOR,
$CH_2S$——$(CH_3)_2$

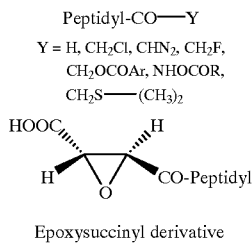

Epoxysuccinyl derivative

SUMMARY OF THE INVENTION

In a search for novel types of cysteine proteinase inhibitors with high selectivity for the cysteine proteinase class of enzymes, a novel class of compounds, having a 1 or 2 amino acid residue group at C-3 of reactive group 3-amino-4-substituted azeridin-2-one, represented by general formula I, have been found. These compounds exhibit an excellent cysteine proteinase inhibitory activity and selectivity among cysteine proteinases.

The present invention is based on the discovery that certain 4-substituted-3-{1 or 2 amino acid residues}-azetidin-2-one derivatives exhibit excellent cysteine proteinase inhibitory activity which can be used for treatment of different diseases such as muscular dystrophy, bone resorption, myocardial infarction or cancer metastasis.

In accordance to the present invention, there is provided 4-substituted-3-{1 or 2 amino acid residue}-azetidin-2-one derivatives of general formula I or pharmaceutically acceptable salts thereof,

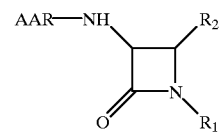

wherein
$R_1$ is selected from the group consisting of hydrogen, $C_1$–$C_6$ alkyl unsubstituded or substituted with 1–2 substituents selected from the group consisting of hydroxy, halogen, cyano, carboxy and amino; —$OR_3$ wherein $R_3$ is a $C_1$–$C_6$ alkyl which may be substituted by 1–2 substituents selected from the group consisting of hydroxy, halogen, cyano, carboxy or amino; and —$SO_3$—$M^+$ wherein M is hydrogen, a metal ion which is selected from the group consisting of sodium, potassium, magnesium, and calcium, or $N^+(R_4)_4$ wherein $R_4$ is $C_1$–$C_6$ alkyl group;
$R_2$ is selected from the group consisting or hydrogen; $C_1$–$C_6$ alkyl, unsubstituted or substituted with 1–2 substituents selected from the group consisting of hydroxy, halogen, cyano, carboxy and amino; —$OCOR_5$ wherein $R_5$ is (i) a $C_1$–$C_6$ alkyl unsubstituted or substituted with 1–2 substituents selected from the group consisting of hydroxy, halogen, cyano, heterocycle, and amino, (ii) $C_2$–$C_4$ alkenyl, (iii) $C_2$–$C_4$ alkynyl, (iv) $C_3$–$C_6$ cycloalkyl, or (v) phenyl which is unsubstituted or substituted by 1–3 substituents selected from the group consisting of hydroxy, halogen, $C_1$–$C_4$ alkyl, $C_1$–$C_2$ alkoxy and or cyano; —$XR_6$ wherein X is O, S, SO, or $SO_2$ and $R_6$ is (i) $C_1$–$C_6$ alkyl unsubstituted or substituted by 1–2 substituents selected from the group consisting of hydroxy, halogen, cyano, heterocycle, and amino, (ii) $C_2$–$C_4$ alkenyl, (iii) $C_2$–$C_4$ alkynyl, (iv) $C_3$–$C_6$ cycloalkyl, (v) phenyl which is unsubstituted or substituted with 1–3 substituents selected from the group consisting of hydroxy, halogen, carboxy, $C_1$–$C_4$ alkyl which is unsubstituted or substituted with at least one of carboxy or amino, $C_1$–$C_2$ alkoxy and cyano, or (vi) heterocycle which may be mono or bicyclic;
a 1–2 amino acid residue wherein the amine is unsubstituted or substituted with group $R_7$. $R_7$ is selected from the group consisting of hydrogen, —$COOR_8$ wherein $R_8$ is (i) $C_1$–$C_6$ alkyl which is unsubstituted or substituted with phenyl, or (ii) phenyl; —$COR_9$ wherein $R_9$ is selected from the group consisting of (i) $C_1$–$C_6$ alkyl which is unsubstituted or substituted by 1–2 substituents selected from the group consisting of hydroxy, halogen, cyano, amino, 4-acetoxyphenyloxy, heterocycle, and phenyl, wherein the phenyl is unsubstituted or substituted by 1–2 substituents selected from halogen, hydroxy, cyano, or amino, (ii) $C_2$–$C_4$ alkenyl which is unsubstituted or substituted with heterocycle or phenyl, wherein the phenyl is unsubstituted or substituted by 1–2 substituents selected from halogen, hydroxy, cyano or amino, (iii) $C_2$–$C_4$ alkynyl, (iv) $C_3$–$C_6$ cycloalkyl, (v) a phenyl group which is unsubstituted or substituted by 1–3 substituents selected from the group consisting of hydroxy, halogen, carboxy, $C_1$–$C_4$ alkyl which is unsubstituted or may be substituted with at least one of carboxy, or amino or both, $C_1$–$C_2$ alkoxy group or cyano, or (vi) a heterocycle which may be mono or bicyclic, —$SO_2R_{10}$ wherein $R_{10}$ is selected from the group consisting of (i) $C_1$–$C_6$ alkyl, (ii) $C_2$–$C_4$ alkenyl which is unsubstituted or substituted with heterocycle or phenyl, (iii) phenyl which is unsubstituted or substituted with 1–3 substituents selected from the group consisting of hydroxy, halogen, carboxy, $C_1$–$C_4$ alkyl group, $C_1$–$C_2$ alkoxy group and cyano, and (iv) naphthyl which is unsubstituted or substituted by 1–3 substituents selected from hydroxy, halogen, cyano, carboxy, $C_1$–$C_4$ alkyl, or $C_1$–$C_2$ alkoxy.

The pharmaceutically acceptable salts of formula I are selected from the group consisting of sodium, potassium, magnesium, calcium, hydrogen chloride, tartaric acid, succinic acid, fumaric acid and p-toluenesulfonic acid.

Examples of $C_1$–$C_6$ alkyl groups as substituents in $R_1$ $R_2$, $R_3$, $R_4$, $R_5$, $R_6$, $R_8$, $R_9$, or $R_{10}$ are straight or branched chain alkyl group having 1–6 carbon atoms such as methyl, ethyl, propyl, 1-methylethyl, butyl, 1-methylpropyl, 2-methylprop-1-yl, 2-methylprop-2-yl, pentyl, 3-methylbutyl, hexyl and the like.

Examples of halogen atoms as substituents in $R_1$ $R_2$, $R_3$, $R_5$, $R_6$, $R_9$, or $R_{10}$, are fluorine, chlorine, bromine or iodine.

Examples of $C_2$–$C_4$ alkenyl group as defined in $R_5$, $R_6$, $R_9$, or $R_{10}$ are alkenyl group having 2–4 carbon atoms such as ethenyl, 1-propenyl, 2-propenyl, 1-butenyl, 3-butenyl and the like.

Examples of $C_2$–$C_4$ alkynyl group as defined in $R_5$, $R_6$, $R_9$, or $R_{10}$ are alkynyl group having 2–4 carbon atoms such as ethynyl, 1-propynyl, 2-propynyl, 1-butynyl, 3-butynyl and the like.

Examples of $C_3$–$C_6$ cycloalkyl groups as defined in $R_5$, $R_6$, or, $R_9$ are cyclopropyl, cyclobutyl, cyclopentyl, or cyclohexyl.

Examples of heterocyclic group or substituents as defined in $R_5$, $R_6$, $R_9$, or $R_{10}$ are $C_2$–$C_{11}$ heterocyclic group which may have 1–3 heteroatoms selected from nitrogen, sulpher or oxygen. Preferred heterocyclic groups are thiophene, pyridine, 1,2,3-triazole, 1,2,4-triazole, quinoline, benzofuran, benzothiophene, morpholine, thiomorpholine, piperazine, piperidine and the like.

Examples of $C_1$–$C_4$ alkyl groups as substituents in $R_5$, $R_6$, $R_9$, or $R_{10}$ are methyl, ethyl, propyl, 2-methyl propyl, butyl, 1,1-dimethyl ethyl and the like.

Examples of $C_1$–$C_2$ alkoxy group as substituents in $R_5$, $R_6$, $R_9$, or $R_{10}$ are methoxy or ethoxy.

The term "amino acid residue" used herein refers to the remaining group after the removal of the hydroxy group from a carboxy group of an amino acid. The term "1–2 amino acid" used herein is one amino acid or one dipeptide consisting of two amino acids which are bonded to each other through a peptide bond.

Examples of amino acids are α-amino acids which are the constituents of normal protein, or their optical isomers, such as glycine, D- or L-alanine, D- or L-valine, D- or L-leucine, D- or L-isoleucine, D- or L-serine, D- or L-threonine, D- or L-aspartic Acid, D- or L-glutamic acid, D- or L-asparagine, D- or L-glutamine, D- or L-lysine, D- or L-arginine, D- or L-phenylalanine, D- or L-phenyl glycine, D- or L-tyrosine, D- or L-methionine, D- or L-hydroxy tyrosine, D- or L-proline and the like.

The azetidinone nucleus carries two asymmetric carbon atoms at position 3 and 4, and can therefore exist as 4-diastereoisomers. In general the preferred isomer is that in which the hydrogen atoms at C3 and C4 are trans to each other this isomer has superior inhibitors activity against different cysteine proteinases such as papain, Cathepsin B, Cathepsin H and Cathepsin L. Such diasterioisomers and their racemic mixtures are also included within use of the azetidinone derivatives as cystein proteinase inhibitors.

DESCRIPTION OF THE PREFERRED EMBODIMENTS

A preferred embodiment of the invention provides 4-substituted-3-{1 or 2 amino acid residue}-azetidin-2-one derivatives of general formula I

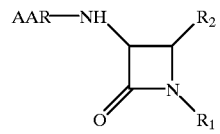

wherein:
$R_1$ is selected from the group consisting of hydrogen, methoxy, 2-carboxy ethoxy, 2-aminoethoxy, 2-carboxy ethyl, 2-aminoethyl and sulphonic acid.

$R_2$ is selected from the group consisting hydrogen, methyl, 2-amino ethyl, 2-carboxy ethyl, acetoxy, butyloxy, 3-methyl propyloxy, 1,1-dimethyl ethoxy, 2-carboxy ethyloxy, 2-aminoethyloxy, 2-fluoro ethoxy, 2-(1,2,3-triazol-4-yl)-ethoxy, cyclopentyloxy, cyclohexyloxy, cyclohexylthio, phenoxy, phenylthio, phenylsulphonyl, 4-(2-carboxy-2-amino ethyl)-phenoxy, 4-carboxy phenoxy, 3-carboxy phenoxy, 2-pyridylthio, 4-pyridylthio and the like.

AAR group is selected from the group consisting of phenylalanine, N-benzyloxy carbonyl phenylalanine, N-(3-phenyl propanoyl)-phenyl alanine, N-acetyl phenylalanine, N-{2-(4-acetoxyphenoxy)-ethanoyl}-phenyl alanine, N-(morpholin-4-yl-carbonyl)-phenyl alanine, N-{3-(morpholin-4-yl)-propanoyl}-phenyl alanine, N-{3-(pyridin-3-yl)-propanoyl}-phenyl alanine, N-(benzofuran-2-yl-carbonyl)-phenyl alanine, N-{3-(thiophen-2-yl)-prop-2-enoyl}-phenyl alanine, N-{4-(1,1-dimethyl ethyl phenyl)-sulphonyl}-phenyl alanine, N-(naphthalen-2-yl-sulphonyl)-phenyl alanine, N-(3-phenyl-prop-2-en-sulphonyl)-phenyl alanine, N-benzyloxy carbonyl leucine, N-benzyloxy carbonyl isoleucine, N-3-phenyl propanoyl leucine, N-3-phenyl propanoyl isoleucine, N-benzyloxy carbonyl proline, N-benzyloxy carbonyl phenyl alanine-glycine and the like.

More specifically, the most preferred embodiments of the present invention include the following compounds:
(3S)-3-(N-benzyloxycarbonyl-L-phenylalanyl)-amino-1-methoxy-azetidin-2-one;
(3S)-3-(N-benzyloxycarbonyl-L-phenylalanyl)-amino-azetidin-2-one;
(3R)-3-(N-benzyloxycarbonyl-L-phenylalanyl)-amino-1-methoxy-azetidin-2-one;
(3R)-B-(N-benzyloxycarbonyl-L-phenylalanyl)-amino-azetidin-2-one;

(3S,4S)-3-(N-benzyloxycarbonyl-L-phenylalanyl)-amino-4-methyl-azetidin-2-one-1-sulfonic acid;
(3S,4S)-3-(N-benzyloxycarbonyl-L-phenylalanyl-glycyl)-amino-4-methyl-azetidin-2-one-1-sulfonic acid;
(3S,4S)-3-(N-benzyloxycarbonyl-L-phenylalanyl)-amino-4-acetoxy-azetidin-2-one;
(3S,4S)-3-(N-benzyloxycarbonyl-L-leucyl)-amino-4-acetoxy-azetidin-2-one;
(3S,4S)-3-(N-acetyl-L-phenylalanyl)-amino-4-acetoxy-azetidin-2-one;
(3S,4S)-3-{N-(3-phenylpropionoyl)-L-phenylalanyl}-amino-4-acetoxy-azetidin-2-one;
(3S,4S)-3-{N-(trans-3-phenylpropenoyl)-L-phenylalanyl}-amino-4-acetoxy-azetidin-2-one;
(3S,4S)-3-{N-(morpholin-4-yl-carbonyl)-L-phenylalanyl}-amino-4-acetoxy-azetidin-2-one;
(3S,4S)-3-{N-(3-morpholin-4-yl-propionoyl)-L-phenylalanyl}-amino-4-acetoxy-azetidin-2-one;
(3S,4S)-3-{N-(3-pyrid-3-yl-propionoyl)-L-phenylalanyl}-amino-4-acetoxy-azetidin-2-one;
(3S,4S)-3-[N-{2-(4-acetoxyphenoxy)-ethnoyl}-L-phenylalanyl]-amino-4-acetoxy-azetidin-2-one;
(3S,4S)-3-{N-(benzofuran-2-yl-carbonyl)-L-phenylalanyl}-amino-4-acetoxy-azetidin-2-one;
(3S,4S)-3-[N-{3-(thiophen-2-yl)-trans-prop-2-enoyl}-L-phenylalanyl]-amino-4-acetoxy-azetidin-2-one;
(3S,4S)-3-[N-{4-(1,1-dimethyl ethyl phenyl)-sulfonyl}-L-phenylalanyl]-amino-4-acetoxy-azetidin-2-one;
(3S,4S)-3-{N-(naphthalen-2-yl-sulfonyl)-L-phenylalanyl}-amino-4-acetoxy-azetidin-2-one;
(3R,4S)-3-(N-benzyloxycarbonyl-L-phenylalanyl)-amino-4-phenylthio-azetidin-2-one;
(3R,4S)-3-(N-benzyloxycarbonyl-L-phenylalanyl)-amino-4-phenylsulfonyl-azetidin-2-one;
(3S,4S)-3-(N-benzyloxycarbonyl-L-phenylalanyl)-amino-4-phenoxy-azetidin-2-one;
(3S,4S)-3-(N-benzyloxycarbonyl-L-phenylalanyl)-amino-4-butyloxy-azetidin-2-one;
(3S,4S)-3-(N-benzyloxycarbonyl-L-phenylalanyl)-amino-4-(2-methyl propyloxy)-azetidin-2-one;
(3S,4S)-3-(N-benzyloxycarbonyl-L-phenylalanyl)-amino-4-(1,1-dimethylethoxy)-azetidin-2-one;
(3S,4S)-3-{N-(3-phenylpropionoyl)-L-phenylalanyl}-amino-4-phenoxy-azetidin-2-one;
(3S,4S)-3-{N-(3-phenylpropionoyl)-L-phenylalanyl}-amino-4-(4-diphenylmethoxy carbonylphenoxy)-azetidin-2-one;
(3S,4S)-3-{N-(3-phenylpropionoyl)-L-phenylalanyl}-amino-4-(4-carboxyphenoxy)-azetidin-2-one;
(3S,4S)-3-{N-(3-phenylpropionoyl)-L-phenylalanyl}-amino-4-(3-carboxyphenoxy)-azetidin-2-one;
(3S,4S)-3-{N-(3-phenylpropionoyl)-L-phenylalanyl}-amino-4-{4-(L-2-benzyloxy-carbonylamino-2-diphenylmethoxycarbonyl ethyl)-phenoxy}-azetidin-2-one;
(3S,4S)-3-(N-(3-phenylpropionoyl)-L-phenylalanyl-amino-4-{4-(L-2-amino-2-carboxy ethyl)-phenoxy}-azetidin-2-one;
(3S,4S)-3-(N-benzyloxycarbonyl-L-phenylalanyl)-amino-4-(4-diphenylmethoxycarbonyl phenoxy)-azetidin-2-one;
(3S,4S)-3-(L-phenylalanyl)-amino-4-(4-carboxyphenoxy)-azetidin-2-one;
(3R,4S)-3-(N-benzyloxycarbonyl-L-phenylalanyl)-amino-4-phenylthio-azetidin-2-one-1-sulfonic acid;
(3S,4S)-3-(N-benzyloxycarbonyl-L-phenylalanyl)-amino-4-acetoxy-azetidin-2-one-1-sulfonic acid;
(3S,4S)-3-(N-benzyloxycarbonyl-L-alanyl)-amino-4-acetoxy-azetidin-2-one; and
(3R,4S)-3-(N-benzyloxycarbonyl-L-phenylalanyl)-amino-4-(pyrid-4-yl-thio)-azetidin-2-one;

Compounds of formula I may be utilized for treatment of different diseases, including muscular dystrophy, cancer metastasis and osteoporosis. The compounds of the invention are most useful to treat cancers which have a high tendency to metastasize, including breast, lung, liver, colon, brain, and prostate. Though not wishing to be restricted to any mechanism of action, the present invention is believed to work by inhibiting the cystein proteinase in medicaments formulated with pharmaceutically acceptable carriers and the compounds of the invention.

DESCRIPTION OF PREFERRED EMBODIMENTS

The present invention relates to the certain 4-substituted-3-{1 or 2 amino acid residue}-azetidin-2-one derivatives having excellent cystein proteinase inhibitory activity and selectivity among cystein proteinase enzymes. The compounds of this invention are characterized by having hydrogen, ester ($OCOR_6$), ether ($OR_6$), or throether ($SP_6$) at position 4 and substituted 1 or 2 amino acid residue group and 1 or 2 amino acid residue mimic aroup at position 3 of azetidin-2-one. Certain derivatives of general formula I were prepared from the common intermediates II by reacting with substituted 1 or 2 amino acid residue carboxylic acios either in presence of dicyclohexylcarbidiime (DCC) or acid chloride in presence of base, or activated ester as shown in scheme I.

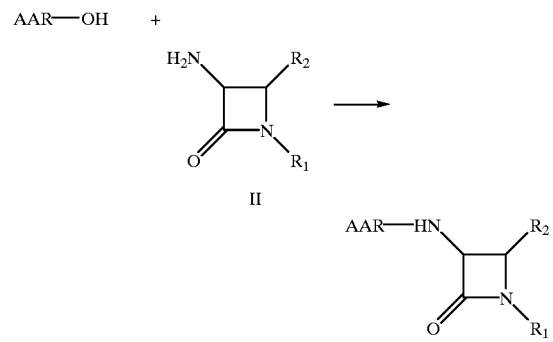

The preparation of compounds II were carried out by following the synthetic route as described in Eur. J. Med. Chem 1992, 27, 131–140, and Tetrahedron 1983, 39, 2577–2589., wherein $R_2$ is hydrogen, $C_1$–$C_6$ alkyl, $C_2$–$C_4$ alkenyl, $C_2$–$C_4$ alkynyl , or $OCOR_5$, and AAR is a 1–2 amino acid residue with a substituent group $COOR_8$. The definition of $R_1$, $R_5$ and $R_8$ are the same as defined above. The alkyl $C_1$–$C_6$ is unsubstituded or substituted with 1–2 substituents selected from the group consisting of halogen, hydroxy, cyano, amino, carboxy, heteroaryl and phenyl.

Certain 4-substituted-3-peptidyl-azetidin-2-one derivatives of general formula I wherein substitutions at the 1 or 2 amino acid residue group are other than $COOR_8$, such as $COR_9$ or $SO_2R_{10}$ were prepared by following the synthetic route as shown in scheme II. The $R_8$, $R_9$ and $R_{10}$ are same as defined above. The benzyloxycarbonyl substituted peptidyl groups were desubstituted and resubstituted through amide bond by reaction with $R_9$—COOH, either in the presence of DCC, or reaction with acid chloride in the presence of base, or reaction with anhydride in the presence of base or activated ester, or through sulphonamide bond by reaction with $R_{10}SO_2Cl$ in the presence of base.

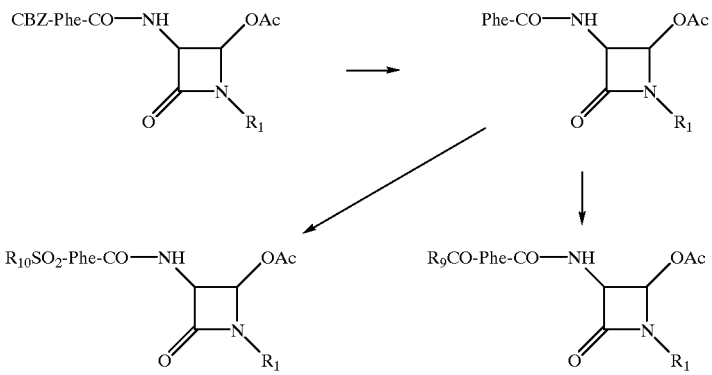

Certain 4-substituted-3-{1 or 2 amino acid residue}-azetidin-2-one derivatives of general formula I wherein $R_2$ is $XR_6$, wherein X is O or S, and $R_6$ is same as defined above, were prepared by following the synthetic route as shown in scheme III starting from a compound of general formula I wherein $R_2$ is $OCOCH_3$. The compound of formula I is reacted with $R_6XH$ in the presence of lewis acids such as zinc acetate, zinc iodide, zinc chloride, titanium tetrachloride, palladium acetate, boron trifluoride, aluminium trichloride and the like. In certain cases where a carboxy group as substituent in $R_6$ is substituted with an $R_{11}$ such as diphenyl methyl or 1,1-dimethyl ethyl, or where an amino group as substituent in $R_6$ is substituted with an $R_{12}$ such as benzyloxy carbonyl or 1,1-dimethyl ethoxy carbonyl, or where both substituted groups as substituents in $R_6$ together were desubstituted by hydrogenation or hydrolysis with acids.

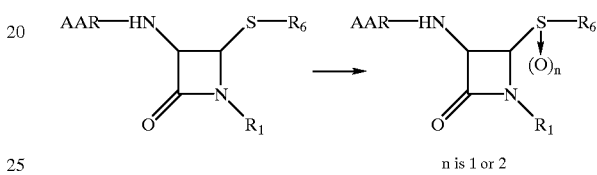

n is 1 or 2

Alternatively, certain 4-substituzed-3-{1 or 2 amino acid residue}-azetidin-2-one derivatives of general formula I wherein $R_1$ is hydrogen were converted to N-surlphonic acid by sulphonation with pyridine-$SO_3$ or dimethylformamide-$SO_3$ complex. The synthetic route is outlined in scheme IV.

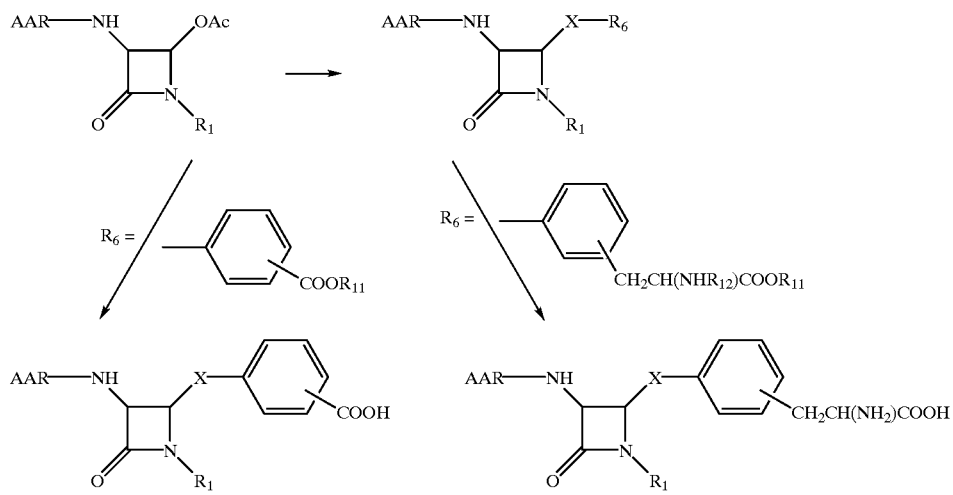

Certain 4-substituted-3-{1 or 2 amino acid residue}-azetidin-2-one derivatives of general formula I wherein $R_2$ is $SR_6$ were converted to $SOR_6$ or $SO_2R_6$ by oxidation with an oxidizing agent selected from the group consisting of m-chloroperbenzoic acid, hydrogen peroxide peracetic acid, potassium permanganate, manganese dioxide and the like. The synthetic route is outlined in scheme III.

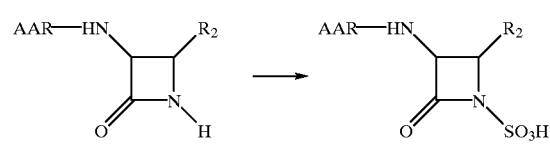

In the above processes, the reactants are reacted together with solvent at elevated or low temperatures for sufficient time to allow the reaction to proceed to completion. The reaction conditions will depend upon the nature and reactivity of the reactants. Wherever a base is used in a reaction, it is selected from the group consisting of triethylamine, pyridine, 4-dimethylaminopyridine, diisoipropylethylamine, 1,5-diazabicyclo[4,3,0]non-5-ene, 1,8-diazabicyclo[5,4,0]undec-7-ene, sodium carbonate, potassium carbonate and cesium carbonate.

Preferred solvents for the reaction are non reactive solvents. Depending on the reactants, a solvent will generally be selected from the group consisting of benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, and the like. Solvent mixtures may also be utilized.

Reaction temperatures generally range from between −70° C. to 150° C. The preferred molar ratio of reactants are 1:1 to 5.0. The reaction time ranges from 0.5 to 72 hours, depending on the reactants.

The desubstitution of N-substitution groups is carried out either by hydrogenation or by hydrolysis with appropriate acids such as hydrochloric acid, trifluoroacetic acid or acetic acid in solvent such as methanol, ethanol, propanol or ethyl acetate. The hydrogenation reaction is usually carried out in the presence of a metal catalyst, such as Pd, Pt, or Rh, under normal pressure to high pressure.

The compounds of this invention, when used alone or in combination with other drugs as an agent for treating muscular dystrophy, osteoporosis or cancer metastasis in mammals including humans, may take pharmaceutical dosage forms including parenteral preparation such as injections, suppositories, aerosols and the like, and oral preparations such as tablets, coated tablets, powders, granules, capsules, liquids and the like. Injections are generally preferred. The above preparations are formulated in a manner known in the art.

For the formulation of solid preparations for oral administration, an excipient, and if desired, a binder, disintegrator, lubricant, coloring agent, corrigent, flavor, etc. is added to the compound of the invention, and then tablets, coated tablets, granules, powders, capsules or the like are prepared in a conventional manner.

For the formulation of injections, a pH adjusting agent, buffer, stabilizer, isotonic agent, local anesthetic or the like is added to the active ingredient of the invention. Injections for subcutaneous, intramuscular or intravenous administration can be prepared in the conventional manner.

For the formulation of suppositories, a base, and, if desired, a surfactant are added to the active ingredient of the invention, and the suppositories are prepared in a conventional manner.

The excipients useful for solid preparations for oral administration are those generally used in the art, such as lactose, sucrose, sodium chloride, starches, calcium carbonate, kaolin, crystalline cellulose, methyl cellulose, glycerin, sodium alginate, gum arabic and the like. Other ingredients which may be used in the formulations of the invention include binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like; lubricants such as magnesium stearate, talc and the like; and additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspensions, solutions, syrups, elixirs and the like, which can be prepared by a conventional way using additives.

The amount of the compound of formula I of the invention to be incorporated into the pharmaceutical composition of the invention varies with the dosage form, solubility and chemical properties of the compound, administration route, administration scheme and the like. Preferably the amount is about 1 to 25 w/w % in the case of oral preparations, and about 0.1 to about 5 w/w % in the case of injections which are parenteral preparations.

The dosage of the compound I of the invention is suitably determined depending on the individual cases taking symptoms, age and sex of the subject and the like into consideration. Usually the dosage in the case of oral administration is about 50 to 1500 mg per day for an adult in 2 to 4 divided doses, and the dosage in the case of injection, for example, by intravenous administration is 2 ml (about 1 to 100 mg) which is administered once a day for adults wherein the injection may be diluted with physiological saline or glucose injection liquid if so desired, and slowly administered over at least 5 minutes. The dosage in case of suppositories is about 1 to 1000 mg which is administered once or twice a day at an interval of 6 to 12 hours wherein the suppositories are administered by insertion into the rectum.

EXAMPLE 1

(3S)-3-(N-benzyloxycarbonyl-L-phenylalanyl)-amino-1-methoxy-azetidin-2-one(1)

A solution of N-(benzyloxycarbonyl)-L-phenylalanine (150 mg, 0.5 mmol) in $CH_2Cl_2$ (10 ml) at −5° C. was treated with triethylamine (0.077 ml, 0.55 mmol) and ethylchloroformate (0.05 ml, 0.5 mmol). The solution was stirred at 0° C. for 30 mins, and treated with (3S)-3-amino-1-methoxy-azetidin-2-one, trifluoroacetic acid salt (115 mg, 0.5 mmol) and pyridine (0.08 ml, 1.0 mmol). The resulting solution was stirred at room temperature overnight. The solvent was removed, and the residue was dissolved in Ethyl acetate (50 ml). The organic layer was washed with cold water (20 ml), brine and dried over sodium sulfate. After removal of solvent, the residue was triturated with ether/hexane (1/1) and gave a pale yellow syrup (130 mg).

Yield: 66%; $^1H$ NMR ($CDCl_3$), δ (ppm): 2.94–3.08 (2H, m), 3.67–3.70 (4H, m) 4.14 (1H, m), 4.38–4.32 (2H, m), 4.92 (1H, d, J=12.4 Hz), 4.99 (1H, d, J=12.4 Hz), 5.40 (1H, d, J=7.9 Hz), 7.03–7.26 (11H, m).

EXAMPLE 2

(3S)-3-(N-benzyloxycarbonyl-L-phenylalanyl)-amino-azetidin-2-one(2)

In a similar manner to the method described in example 1, the title compound was obtained by reacting (3S)-3-amino-azetidin-2-one, trifluoroacetic acid salt with the ethoxy anhydride of N-(benzyloxycarbonyl)-L-phenylalanine.

Yield: 94%; $^1H$ NMR ($CDCl_3$), δ (ppm): 3.10 (2H, m), 4.45 (1H, m), 4.57 (1H, m), 5.00–5.15 (3H, m), 5.30 (1H, s), 5.65 (1H, bs), 7.05–7.48 (11H, m), 8.66 (1H, s).

EXAMPLE 3

(3R)-3-(N-benzyloxycarbonyl-L-phenylalanyl)-amino-1-methoxy-azetidin-2-one(3)

In a similar manner to the method described in example 1, the title compound was obtained by reacting (3R)-3-amino-1-methoxy-azetidin-2-one, trifluoroacetic acid salt with the ethoxy anhydride of N-(benzyloxycarbonyl)-L-phenylalanine.

Yield 93%; $^1$H NMR (CDCl$_3$), δ (ppm): 2.99 (1H, s), 3.03 (1H, s), 3.65–3.17 (5H, m), 4.10 (1H, m), 4.64 (1H, m), 5.00 (2H, s), 5.37 (1H, bs), 6.78 (1H, d, J=6.8 Hz), 7.23 (10 H, m).

EXAMPLE 4

(3R)-3-(N-benzyloxycarbonyl-L-phenylalanyl)-amino-azetidin-2-one(4)

IN a similar manner to the method described in example 1, the title compound was obtained by reacting (3R)-3-amino-azetidin-2-one, trifluoroacetic acid salt with the ethoxy anhydride of N-(benzyloxycarbonyl)-L-phenylalanine.

Yield: 10%; $^1$H NMR (CDCl$_3$), δ (ppm): 3.11 (3H, m), 4.63 (1H, m), 5.07 (3H, m), 5.30 (1H, m), 7.05–7.40 (13H, m)

EXAMPLE 5

Potassium (3S,4S)-3-(N-benzyloxycarbonyl-L-phenylalanyl)-amino-4-methyl-azetidin-2-one-1-sulfonate (5)

A mixture of potassium (3S,4S)-3-amino-4-methyl-azetidin-2-one-1-sulfonate (162 mg, 0.744 mmol), N-(benzyloxycarbonyl)-L-phenylalanine (223 mg, 0.744 mmol), DCC (153 mg, 0.744 mmol) and HOBt (100 mg, 0.744 mmol) in DMF (10 ml) was stirred at r.t overnight. DMF was removed in vacuum, and the residue was taken up in water (50 ml) and washed with methyl isobutyl ketone (3×50 ml) and hexane (50 ml). The aqueous portion was freeze-dried and purified by reversed-phase HPLC, giving an analytically pure white solid (49 mg).

Yield: 13%; m.p.: 300° C. (dec.); Negative FAB-MS: 460 (M–K)$^-$, calcd for C$_{21}$H$_{22}$O$_7$N$_3$SK 499; IR(KBr, cm$^-$): 3285, 1760, 1700, 1670, 1530, 1240, 1040; $^1$H NMR (D$_2$O), δ (ppm): 1.45 (3H, d, J=6.3 Hz), 3.03 (2H, m) 4.02 (1H, m), 4.34 (2H, m), 5.01 (1H, d, J=12.5 Hz), 5.11 (1H, d, J=12.5 Hz), 7.24–7.40 (10 H, m).

EXAMPLE 6

Potassium (3S,4S)-3-(N-benzyloxycarbonyl-L-phenylalanyl-glycinyl)-amino-4-methyl-azetidin-2-one-1-sulfonate (6)

In a manner analogous to the method described in example 5, the title compound was obtained by using CBZ-Phe-Gly-OH as a starting material.

Yield: 11%; m.p.: 300° C. (dec.); Negative FAB-MS: 517 (M–K)$^-$, calcd for C$_{23}$H$_{25}$O$_8$N$_4$SK 556; IR (KBr, cm$^-$): 3430, 1770, 1670, 1560, 1250; $^1$H NMR (D$_2$O), δ (ppm): 1.49 (3H, d, J=6.3 Hz), 2.96 (1H, dd, d, J=17.1 Hz), 3.95 (1H, d, J=17.1 Hz), 4.10 (1H, m), 4.40 (2H, m), 5.09 (1H, d, J=12.5 Hz), 5.11 (1H, d, J=12.5 Hz), 7.24–7.43 (10 H, m).

EXAMPLE 7

(3S,4S)-3-(N-benzyloxycarbonyl-L-phenylalanyl)-amino-4-acetoxy-azetidin-2-one (7)

(3S,4S)-3-benzyloxycarbonylamino-4-acetoxy-azetidin-2-one (5.56 g, 20 mmol) was hydrogenated with 5 g of 10% palladium on activated carbon in 100 ml of ethyl acetate at 50 psi hydrogen pressure at room temperature for 1.5 hrs. After removal of catalyst by filtration, desubstituted (3S,4S)-3-amino-4-acetoxy-azetidin-2-one in ethyl acetate was obtained.

To a solution of N-benzyloxycarbonyl-L-phenylalanine (5.98 g, 20 mmol) and triethylamine (2.02 g, 20 mmol) in chloroform (100 ml), ethyl chloroformate (2.18 g, 20 mmol) was added at –15° C. The reaction mixture was stirred at a bath temperature of –10 to 5° C. for 1.5 hrs. Then a precooled (ca. –15° C.) solution of (3S,4S)-3-amino-4-acetoxy-azetidin-2-one in ethyl acetate, which was obtained from hydrogenation of (3S,4S)-3-benzyloxycarbonylamino-4-acetoxy-azetidin-2-one (see above), was added at –15° C. and stirring was continued at a bath temperature of –15 to 5° C. for 1 hr. After removal of solvent, the residue was dissolved in ethyl acetate, washed with water, brine and dried over sodium sulfate. After removal of solvent, the residue was purified by silica gel column chromatography using hexane-ethyl acetate (1:2) as eluent and the title compound was obtained as white solid.

Yield: 78%; m.p.: 175–177° C.; FAB-MS: 426 (MH$^+$), calcd for C$_{22}$H$_{23}$N$_3$O$_6$ 425 IR (KBr, cm$^{-1}$): 3315, 1797, 1740, 1680, 1660, 1533, 1258, 1227; $^1$H NMR(DMSO-d$_6$), δ (ppm): 2.10 (3H, s), 2.78 (1H, dd, J=14, 10), 3.02 (1H, dd, J=14, 4), 4.26 (1H, m), 4.64 (1H, d, J=8), 4.95 (2H, m), 5.76 (1H, s), 7.15–7.35 (10 H, m), 7.60 (1H, d, J=8), 8.83 (1H, d, J=8), 9.20 (1H, s).

EXAMPLE 8

(3S,4S)-3-(N-benzyloxycarbonyl-L-leucyl)-amino-4-acetoxy-azetidin-2-one (8)

By a manner analogous to the method described in example 7, the title compound was obtained by reacting N-benzyloxycarbonyl-L-leucine with (3S,4S)-3-amino-4-acetoxy-azetidin-2-one.

Yield: 40%; m.p.: 70–80° C. (dec.); FAB-MS: 392 (MH$^+$), calcd for C$_{19}$H$_{25}$N$_3$O$_6$ 391; IR (KEr, cm$^{-1}$): 3325, 1790, 1720, 1540, 1230, 1040; $^1$H NMR(CDCl$_3$), δ (ppm): 0.91 (6H, m), 1.48–1.68 (3H, m), 2.09 (3H, s), 4.27 (1H, m), 4.70 (1H, d, J=7.4 Hz), 5.10 (2H, m), 5.66 (1H, bs), 5.80 (1H, s), 7.33 (6H, m), 7.59 (1H, bs).

EXAMPLE 9

3S,4S)-3-(N-acetyl-L-phenylalanyl)-amino-4-acetoxy-azetidin-2-one (9)

(3S,4S)-3-(N-benzyloxycarbonyl-L-phenylalanyl)-amino-4-acetoxy-azetidin-2-one (850 mg, 2 mmol) obtained in example 7, was hydrogenated with 500 mg of 100 palladium on activated carbon in 60 ml of ethyl acetate at 50 psi hydrogen pressure at room temperature for 4 hrs in the presence of acetic anhydride (255 mg, 2.5 mmol). After filtration of the catalyst and removal of solvent, a white solid was collected and washed with ethyl acetate, diethyl ether and dried in air. 600 mg of title compound was obtained as white solid.

Yield: 90%; m.p.: 190–191° C.; FAB-MS: 334 (MH$^+$), calcd for C$_{16}$H$_{19}$N$_3$O$_5$ 333; IR (KBr, cm$^{-1}$): 3380, 1800, 1751, 1647, 1529, 1370, 1219; $^1$H NMR(DMSO-d$_6$), δ (ppm): 1.77 (3H, s), 2.09 (3H, s), 2.75 (1H, dd, J=14, 10), 3.01 (1H, dd, J=14, 5), 4.49 (1H, m), 4.59 (1H, dd, J=8, 1), 5.74 (1H, d, J=1), 7.15–7.30 (5H, m), 8.15 (1H, d, J=8), 8.72 (1H, d, J=8), 9.16 (1H, s).

EXAMPLE 10

(3S,4S)-3-{N-(3-phenylpropionoyl)-L-phenylalanyl}-amino-4-acetoxy-azetidin-2-one (10)

(3S,4S)-3-(N-benzyloxycarbonyl-L-phenylalanyl)-amino-4-acetoxy-azetidin-2-one (1.70 g, 4 mmol) obtained in example 7, was hydrogenated with 3.5 g of 10% palladium on activated carbon in 200 ml of ethyl acetate at 50 psi hydrogen pressure at room temperature for 2 hrs. After removal of catalyst by filtration, the deprotected (3S,4S)-3-(L-phenylalanyl)-amino-4-acetoxy-azetidin-2-one in ethyl acetate was obtained.

To a solution of 3-phenylpropionic acid (630 mg, 4 mmol) and triethylamine (425 mg, 4.2 mmol) in chloroform (80 ml), ethyl chloroformate (436 mg, 4 mmol) was added at –15° C. The reaction mixture was stirred at a temperature of −10 to 5° C. for 2 hrs. Then a precooled (ca. −15° C.) solution of (3S,4S)-3-(L-phenylalanyl)-amino-4-acetoxy-azetidin-2-one in ethyl acetate, which was obtained from hydrogenation of (3S,4S)-3-(N-benzyloxycarbonyl-L-phenylalanyl)-amino-4-acetoxy-azetidin-2-one (see above), was added at −15° C. under stirring at a bath temperature of −15 to 5° C. The resulting solution was stirred for 1 hr and concentrated. The residue was dissolved in ethyl acetate, washed with a saturated solution of $NaHCO_3$, water, brine and dried over sodium sulfate. After removal of solvent, the residue was purified by silica gel column chromatography using hexane-ethyl acetate (1:2) as eluent and the title compound (1.1 g) was obtained as a white solid.

Yield: 65%; m.p.: 144.5–146.2° C.; FAB-MS: 424 (MH$^+$), calcd for $C_{23}H_{25}N_3O_5$ 423; IR (KBr, cm$^{-1}$): 3380, 1803, 1749, 1644, 1535, 1218; $^1$H NMR(DMSO-d$_6$), δ (ppm): 2.09 (3H, s), 2.36 (2H, m), 2.68 (2H, m), 2.75 (1H, dd, J=14, 10), 3.01 (1H, dd, J=14, 5), 4.53 (1H, m), 4.60 (1H, dd, J=8, 1), 5.75 (1H, d, J=1), 7.05–7.30 (10H, m), 8.15 (1H, d, J=8), 8.72 (1H, d, J=8), 9.17 (1H, s).

EXAMPLE 11

(3S,4S)-3-{N-(trans-3-phenylpropenoyl)-L-phenylalanyl}-amino-4-acetoxy-azetidin-2-one (11)

(3S,4S)-3-(N-benzyloxycarbonyl-L-phenylalanyl)-amino-4-acetoxy-azetidin-2-one (200 mg, 0.47 mmol) obtained in example 7, was hydrogenated with 300 mg of 10% palladium on activated carbon in 50 ml of ethyl acetate at 50 psi hydrogen pressure at room temperature for 2 hrs. After removal of catalyst by filtration, the desubstituted (3S,4S)-3-(L-phenylalanyl)-amino-4-acetoxy-azetidin-2-one in ethyl acetate was cooled to −15 ° C. Then triethylamine (50 mg, 0.5 mmol) and trans-β-styrenesulfonyl chloride (95 mg, 0.47 mmol) were added at −15 ° C. Stirring was continued at a bath temperature of −10 to 5° C. for 2 hr. The reaction mixture was diluted with ethyl acetate, washed with water, brine and dried over sodium sulfate. After removal of solvent, the residue was purified by silica gel column chromatography using hexane-ethyl acetate (1:1) as eluent and the title compound (200 mg) was obtained as a white solid.

Yield: 93%; m.p.: 103–105° C.; IR (KBr, cm-1): 3315, 1785, 1748, 1672, 1523, 1321, 1227; $^1$H NMR(DMSO-d$_6$), δ (ppm): 2.03 (3H, s), 2.77 (1H, dd, J=14, 10), 2.92 (1H, dd, J=14, 5), 3.99 (1H, m), 4.57 (1H, d, J=8), 5.59 (1H, s), 6.55 (1H, d, J=16), 7.10–7.55 (1H, m), 7.94 (1H, d, J=8), 8.86 (1H, d, J=8), 9.19 (1H, s).

EXAMPLE 12

(3S,4S)-3-{N-(morpholin-yl-carbonyl)-L-phenylalaninyl}-amino-4-acetoxy-azetidin-2-one (12)

By a method similar to the method described in example 7, the title compound was obtained by reacting N-(morpholin-yl-carbonyl)-L-phenylalanine with (3S,4S)-3-amino-4-acetoxy-azetidin-2-one.

Yield: 10%; m.p.: 160.7–162.3° C.; FAB-MS: 405 (MH$^+$), calcd for $C_{19}H_{24}N_4O_6$ 404; IR (KBr, cm$^{-1}$): 3380, 1787, 1748, 1668, 1623, 1535, 1224; $^1$H NMR(DMSO-d$_6$), δ (ppm): 2.09 (3H, s), 2.83 (1H, dd, J=14, 10), 3.01 (1H, dd, J=14, 4), 3.21 (4H, m), 3.45 (4H, m), 4.35 (1H, m), 4.64 (1H, d, J=1), 5.77 (1H, d, J=1), 6.65 (1H, d, J=8), 7.15–7.28 (5H, m), 8.67 (1H, d, J=8), 9.17 (1H, s).

EXAMPLE 13

(3S,4S)-3-{N-(3-morpholin-4-yl-propionoyl-L-phenylalanyl}-amino-4-acetoxy-azetidin-2-one (13)

By a method similar to the method described in example 10, the title compound was obtained by reacting 3-morpholin-4-yl-propionic acid with (3S,4S)-3-(L-phenylalanyl)-amino-4-acetoxy-azetidin-2-one.

Yield: 38%; m.p.: 85° C. (dec.); FAB-MS: 433 (MH$^+$), calcd for $C_{21}H_{28}N_4O_6$ 432; IR (KBr, cm$^{-1}$): 3285, 1780, 1750, 1650, 1540, 1450, 1370, 1220; $^1$H NMR(CDCl$_3$), δ (ppm): 2.12 (3H, s), 2.40 (8H, m), 3.03 (1H, dd, J=9.2 & 13.8 Hz), 3.22 (1H, dd, J=5.1 & 13.8 Hz), 3.60 (4H, m), 4.61 (1H, d, J=6.4 Hz), 4.75 (1H, dd, J=7.8 & 14.0 Hz), 5.86 (1H, s), 7.0 (1H, s), 7.26 (5H, m), 7.49 (1H, d, J=7.7 Hz), 8.83 (1H, d, J=7.5 Hz).

EXAMPLE 14

(3S,4S)-3-{N-(3-pyrid-3-yl-propionoyl)-L-phenylalanyl}-amino-4-acetoxy-azetidin-2-one (14)

By a method similar to the method described in example 10, the title compound was obtained by reacting 3-(pyrid-3-yl)-propionic acid with (3S,4S)-3-(L-phenylalanyl) amino-4-acetoxy-azetidin-2-one.

Yield: 30%; m.p.: 150° C. (dec.); FAB-MS: 425 (MH$^+$), calcd for $C_{22}H_{24}N_4O_5$ 424; IR (KBr, cm$^{-1}$): 3310, 1790, 1740, 1660, 1540, 1370, 1230; $^1$H NMR(DMSO-d$_6$), δ (ppm): 2.10 (3H, s), 2.40 (2H, t, J=7.7 Hz), 2.72 (2H, t, J=7.7 Hz), 2.82 (1H, dd, J=9.4 & 14.0 Hz), 3.00 (1H, dd, J=5.2 & 13.9 Hz), 4.54 (1H, m), 4.60 (1H, d, J=8.4 Hz), 5.74 (1H, s), 7.22 (6H, m), 7.50 (1H, d, J=7.0 Hz), 8.18 (1H, d, J=8.8 Hz), 8.37 (2H, m), 8.74 (1H, d, J=7.8 Hz), 9.18 (1H, s).

EXAMPLE 15

(3S,4S)-3-[N-{2-(4-acetoxyphenoxy)-ethanoyl}-L-phenylalanyl]-amino-4-acetoxy-azetidin-2-one (15)

By a method similar to the method described in example 10, the title compound was obtained by reacting 4-acetoxyphenoxy acetic acid with (3S,4S)-3-(L-phenylalanyl) amino-4-acetoxy-azetidin-2-one.

Yield: 34%; m.p.: 190° C.; FAB-MS: 506 (MNa$^+$), calcd for $C_{24}H_{25}N_3O_8$ 483; IR (KBr, cm$^{-1}$): 3295, 1800, 1660, 1600, 1530, 1225; $^1$H NMR(DMSO-d$_6$), δ (ppm): 2.10 (3H, s), 2.52 (3H, s), 2.98 (1H, dd, J=9.2 & 13.8 Hz), 3.09 (1H, dd, J=5.2 & 13.8 Hz), 4.56 (2H, s), 4.58 (1H, m), 4.63 (1H, d, J=8.1 Hz), 5.76 (1H, s), 6.89 (2H, d, J=8.8 Hz), 7.23 (5H, s), 7.87 (2H, d, J=8.8 Hz), 8.33 (1H, d, J=8.5 Hz), 8.83 (1H, d, J=8.5 Hz), 9.20 (1H, s).

EXAMPLE 16

(3S,4S)-3{N-(benzofuran-2-yl-carbonyl)-L-phenylalanyl}-amino-4-acetoxy-azetidin-2-one (16)

By a method similar to the method described in example 10, the title compound was obtained by reacting 2-benzofurancarboxylic acid with (3S,4S)-3-(L-phenylalanyl) amino-4-acetoxy-azetidin-2-one.

Yield: 50%; m.p.: 115° C. (dec.); FAB-MS: 436 (MH$^+$), calcd for $C_{23}H_{21}N_3O_6$ 435; IR (KBr, cm$^{-1}$): 3295, 1790, 1750, 1650, 1520, 1370, 1220; $^1$H NMR(CDCl$_3$), δ (ppm): 2.03 (3H, s), 3.23 (2H, m), 4.75 (1H, d, J=8.0 Hz), 5.07 (1H, dd, J=5.8 & 13.8 Hz), 5.77 (1H, s), 7.23 (5H, m), 7.47 (3H, m), 7.60 (3H, m), 8.08 (1H, d, J=15 6.8 Hz).

EXAMPLE 17

(3S,4S)-3-[N-{3-(thiophen-2-yl)-trans-prop-2-enoyl}-L-phenylalanyl]-amino-4-acetoxy-azetidin-2-one (17)

By a method similar to the method described in example 10, the title compound was obtained by reacting 2-thiopheneacrylic acid with (3S,4S)-3-(L-phenylalanyl)-amino-4-acetoxy-azetidin-2-one.

Yield: 54%; m.p.: 220–221° C.; FAB-MS: 428 (MH$^+$), calcd for $C_{21}H_{21}N_3O_5S$ 427; IR (KBr, cm$^{-1}$): 3285, 1775, 1750, 1640, 1620, 1540, 1210; $^1$H NMR(DMSO-d$_6$), δ (ppm): 2.07 (3H, s), 2.80 (1H, dd, J=9.2 & 13.8 Hz), 3.05

(1H,dd, J=5.1 & 13.8 Hz), 4.60 (1H, d, J=8.4 Hz), 4.62 (1H, m), 5.75 (1H, s), 6.44 (1H, d, J=14.7 Hz), 7.07 (1H, d, J=4.2 Hz), 7.23 (5H, m), 7.34 (1H, d, J=4.2 Hz), 7.52 (1H, d, J=14.7 Hz), 7.60 (1H, d, J=4.7 Hz), 8.42 (1H, d, J=8.8 Hz), 8.82 (1H, d, J=7.8 Hz), 9.16 (1H, s).

EXAMPLE 18
3S,4S)-3-[N-{4-(1,1-dimethyl ethyl) phenyl sulfonyl}-L-phenylalanyl]-amino-4-acetoxy-azetidin-2-one (18)

By a method similar to the method described in example 11, the title compound was obtained by reacting 4-(1,1-dimethyl ethyl)-phenylsulfonyl chloride with (3S,4S)-3-(L-phenylalanyl)-amino-4-acetoxy-azetidin-2-one.

Yield: 74%; m.p.: 125° C. (dec.); FAB-MS: 510 (MNa$^+$), calcd for $C_{24}H_{29}N_3O_6S$ 487; IR (KBr, cm$^{-1}$): 3295, 1780, 1750, 1660, 1520, 1330, 1225; $^1$H NMR(Acetone-d$_6$), δ (ppm): 1.34 (9H, s), 2.08 (3H, s), 2.84 (1H, dd, J=9.2 & 13.8 Hz), 3.03 (1H, dd, J=5.7 & 13.8 Hz), 4.10 (1H, m), 4.67 (1H, dd, J=1.3 & 7.8 Hz), 5.81 (1H, d, J=1.1 Hz), 6.67 (1H, d, J=8.9 Hz), 7.13 (5H, m), 7.48 (2H, d, J=8.6 Hz), 7.60 (2H, d, J=8.6 Hz), 8.06 (1H, d, J=7.7 Hz), 8.17 (1H, s).

EXAMPLE 19
(3S,4S)-3-{N-(naphthalen-2-yl-sulfonyl)-L-phenylalanyl}-amino-4-acetoxy-azetidin-2-one (19)

By a method similar to the method described in example 11, the title compound was obtained by reacting 2-naphthalenesulfonyl chloride with (3S,4S)-3-(L-phenylalanyl) amino-4-acetoxy-azetidin-2-one.

Yield: 42%; m.p.: 174–176° C.; FAB-MS: 482 (MH$^+$), calcd for $C_{24}H_{23}N_3O_6S$ 481; IR (KBr, cm$^{-1}$): 3330, 1780, 1750, 1670, 1320, 1225; $^1$H NMR(CDCl$_3$), δ (ppm): 2.09 (3H, s), 2.83 (1H, dd, J=9.2 & 14.1 Hz), 3.06 (1H, dd, J=4.7 & 14.1 Hz), 4.04 (1H, m), 4.83 (1H, d, J=7.8 Hz), 5.90 (1H, s), 5.95 (1H, s), 6.78 (5H, m), 7.26 (1H, s), 7.48–7.98 (7H, m), 8.20 (1H, s).

EXAMPLE 20
(3R,4S)-3-(N-benzyloxycarbonyl-L-phenylalanyl)-amino-4-phenylthio-azetidin-2-one (20)

A mixture of (3S,4S)-3-(N-benzyloxycarbonyl-L-phenylalanyl)-amino-4-acetoxy-azetidin-2-one (500 mg, 1.18 mmol) obtained in example 7, thiophenol (117 mg, 1.07 mmol), and zinc acetate dihydrate (207 mg, 0.95 mmol) in a mixture of benzene (20 ml) and toluene (20 ml) was refluxed for 4 hrs using Dean-Stark water separator. After cooling, the reaction mixture was partitioned between ethyl acetate, containing a small volume of acetone, and water. The organic layer was washed with water, brine and dried over sodium sulfate. After removal of the solvent to dryness, a white solid was washed with dichloromethane and 410 mg of the title compound was obtained as a white solid.

Yield: 73%; m.p.: 174–175.5° C.; FA3-MS: 476 (MH$^+$), calcd for $C_{26}H_{25}N_3O_4S$ 475; IR (KBr, cm$^{-1}$): 3300, 1772, 1683, 1522, 1240; $^1$H NMR(DMSO-d$_6$), δ (ppm): 2.77 (1H, dd, J=14, 10), 3.02 (1H, dd, J=14, 5), 4.26 (1H, m), 4.58 (1H, dd, J=8, 2), 4.9 (3H, m), 7.10–7.50 (15H, m), 7.58 (1H, d, J=8), 8.90 (1H, d, J=8), 9.03 (1H, s).

EXAMPLE 21
(3R,4S)-3-(N-benezyloxycarbonyl-phenylalanyl)-amino-4-phenylsulfonyl-azetidin-2-one (21)

A mixture of (3R,4R)-3-(N-benzyloxycarbon-L-phenylalanyl)-amino-4-phenylthio-azetidin-2-one (540 mg, 1.136 mmol) obtained in example 20, and 3-chloroperoxybenzoic acid (588 mg, 3.42 mmol) in dichloromethane (400 ml) was stirred at room temperature for 9 hrs. After removal of dichloromethane, the reaction mixture was partitioned between ethyl acetate and water, the organic layer was washed with water, brine, and dried over sodium sulfate. After removal of the solvent to dryness, a white solid was washed with dichloromethane and 450 mg of the title compound was obtained as a white solid.

Yield: 78%; m.p.: 200° C. (dec.); FAB-MS: 508 (MH$^+$), calcd for $C_{26}H_{25}N_3O_6S$ 507; IR (KBr, cm$^{-1}$): 3310, 1800, 1680, 1525, 1300, 1240; $^1$H NMR(DMSO-d$_6$), δ (ppm): 2.71 (1H, dd, J=9.1 & 13.8 Hz), 2.96 (1H, dd, J=5.0 & 13.8 Hz), 4.21 (1H, m), 4.93 (4H, m), 7.26 (10H, m), 7.60 (1H, d, J=7.8 Hz), 7.55–7.94 (5H, m), 8.92 (1H, d, J=7.8 Hz), 9.32 (1H, s).

EXAMPLE 22
(3S,4S)-3-(N-benzyloxycarbonyl-L-phenylalanyl)-amino-4-phenoxy-azetidin-2-one (22)

By a method similar to the method described in example 20, the title compound was obtained as a white solid by reacting phenol with (3S,4S)-3-(N-benzyloxycarbonyl-L-phenylalanyl)-amino-4-acetoxy-azetidin-2-one.

Yield: 22%; FAB-MS: 460 (MH$^+$), calcd for $C_{26}H_{25}N_3O_5$ 459; IR (KBr, cm$^{-1}$): 3325, 3190, 1776, 1711, 1664, 1545, 1241; $^1$H NMR(DMSO-d$_6$), δ (ppm): 2.81 (1H, dd, J=9.1 & 13.9 Hz), 3.05 (1H, dd, J=5.1 & 13.9 Hz), 4.28 (1H, m), 4.70 (1H, d, J=9.0 Hz), 4.98 (2H, s), 5.53 (1H, s), 7.15–7.35 (10H, m), 7.67 (1H, d, J=8.4 Hz), 8.97 (1H, d, J=8.9 Hz), 9.34 (1H, s).

EXAMPLE 23
(3S,4S)-3-(N-benzyloxycarbonyl-L-phenylalanyl)-amino-4-butyloxy-azetidin-2-one (23)

By a method similar to the method described in example 20, the title compound was obtained by reacting 1-butanol with (3S,4S)-3-(N-benzyloxycarbonyl-L-phenylalanyl)-amino-4-acetoxy-azetidin-2-one.

Yield: 14%; m.p.: 162–164° C.; FAB-MS: 440 (MH$^+$), calcd for $C_{24}H_{29}N_3O_5$ 439; IR (KBr, cm$^{-1}$): 3300, 1790, 1690, 1660, 1540; $^1$H NMR(CDCl$_3$), δ (ppm): 0.89 (3H, t, J=7.4 Hz), 1.28 (2H, m), 1.49 (2H, m), 3.10 (2H, d, J=6.4 Hz), 3.43 (2H, m), 4.46 (1H, dd, J=7.0 & 14.6 Hz), 5.06 (3H, m), 5.35 (2H, m), 6.55 (1H, bs), 6.72 (1H, bs), 7.15–7.40 (10H, m).

EXAMPLE 24
(3S,4S)-3-(N-benzyloxycarbonyl-L-phenylalanyl)-amino-4-(2-methyl propyloxy)-azetidin-2-one (24)

By a method similar to the method described in example 20, the title compound was obtained by reacting 2-methyl-1-propanol with (3S,4S)-3-(N-benzyloxycarbonyl-L-phenylalanyl)-amino-4-acetoxy-azetidin-2-one.

Yield: 7%; $^1$H NMR(Acetone-d$_6$), δ (ppm): 0.88 (6H, d=6.6 Hz), 1.85 (1H, m), 2.94 (1H, dd, J=9.6 & 13.8 Hz), 3.26 (1H, dd, J=4.6 & 13.8 Hz), 3.29 (2H, d, J=6.7 Hz), 4.57 (1H, m), 5.00 (2H, s), 5.15 (1H, d, J=3.9 Hz), 5.30 (1H, m), 6.48 (1H, bd, J=8.4 Hz), 7.17–7.37 (10H, m), 7.76 (1H, d, J=9.1 Hz), 8.08 (1H, s).

EXAMPLE 25
(3S,4S)-3-(N-benzyloxycarbonyl-L-phenylalanyl)-amino-4-(1,1-dimethyl ethoxy)-azetidin-2-one (25)

BY a method similar to the method described in example 20, the title compound was obtained by reacting 1,1-dimethyl ethanol with (3S,4S)-3-(N-benzyloxycarbonyl-L-phenylalanyl)-amino-4-acetoxy-azetidin-2-one.

Yield: 14%; $^1$H NMR(CDCl$_3$), δ (ppm): 1.17 (9H, s), 3.10 (2H, d, J=6.8 Hz), 4.45 (1H, dd, J=7.0 & 14.6 Hz), 5.08 (2H, s), 5.31 (3H, m), 6.39 (2H, s), 7.20–7.40 (10H, m).

EXAMPLE 26
(3S,4S)-3-{N-(3-phenylpropionoyl)-L-phenylalanyl}-amino-4-phenoxy-azetidin-2-one (26)

A mixture of (3S,4S)-3-{(N-(3-phenylpropionoyl)-L-phenylalanyl}-amino-4-acetoxy-azetidin-2-one (212 mg, 0.5 mmol) obtained in example 10, phenol (41 mg, 0.45 mmol), and zinc acetate dihydrate (110 mg, 0.5 mmol) in a mixture of benzene (8 ml) and toluene (8 ml) was refluxed for 5.5 hrs using Dean-Stark water separator. The reaction mixture was purified by silica gel column chromatography using hexane-ethyl acetate (2:1) as eluent and the title compound (50 mg) was obtained as a white solid.

Yield: 22%; m.p.: 199–201 ° C. (dec.); FAB-MS: 458 (MH$^+$), calcd for $C_{27}H_{27}N_3O_4$ 457; IR (KBr, cm$^{-1}$): 3290, 1782, 1641, 1538, 1491, 1225; $^1$H NMR(DMSO-d$_6$), δ (ppm) 2.37 (2H, m), 2.55–3.10 (4H, m), 4.54 (1H, m), 4.64 (1H, d, J=8), 5.51 (1H, s), 6.80–7.40 (15H, m), 8.23 (1H, d, J=8), 8.85 (1H, d, J=8), 9.32 (1H, s).

EXAMPLE 27

(3S,4S)-3-{N-(3-phenylpropionoyl)-L-phenylalanyl}-amino-4-{4-(diphenylmethoxycarbonyl)-phenoxy}-azetidin-2-one (27A) and (3S,4S)-3-{N-(3-phenylpropionoyl)-L-phenylalanyl}-amino-4-(4-carboxyphenoxy)-azetidin-2-one (27B)

BY a method similar to the method described in example 26, the protected title compound (27A) was obtained as a white solid by reacting 4-(diphenylmethoxycarbonyl)-phenol with (3S,4S)-3-{N-(3-phenylpropionoyl)-L-phenylalanyl}-amino-4-acetoxy-azetidin-2-one prepared from example 10.

300 mg of the substituted compound was hydrogenated with 600 mg of 5% palladium on activated carbon in 30 ml ethyl acetate at 50 psi hydrogen pressure at room temperature for 3 hrs. The catalyst was filtered and washed with ethyl acetate, and the combined filtrates were evaporated in vacuo. The residue was triturated with ether and the supernatant was decanted. The remaining solid was dried under vacuum to give white solid (120 mg).

The title compound (27B) was converted to sodium salt with NaHCO$_3$ (1 equivalent) in CH$_3$CN/H$_2$O for 0.5 h followed by freeze-drying.

Yield: 15%; m.p.: 217° C. (dec.); IR (KBr, cm$^{-1}$): 3400, 3290, 1700, 1650, 1600, 1540, 1380, 1230; $^1$H NMR (DMSO-d$_6$), δ (ppm): 2.39 (2H, t, J=7.7 Hz), 2.73 (2H, t, J=7.7 Hz), 2.80 (1H, dd, J=9.2 & 13.8 Hz), 3.05 (1H, dd, J=5.1 & 13.8 Hz), 4.51 (1H, m), 4.79 (1H, d, J=8.4 Hz), 5.6 (1H, s), 6.76 (2H, t, J=8.6 Hz), 7.2 (10H, m), 7.86 (2H, d, J=8.6 Hz), 8.28 (1H, d, J=7.9 Hz), 9.4 (2H, s), 9.5 (1H, s).

EXAMPLE 28

(3S,4S)-3-{N-(3-phenylpropionoyl)-L-phenylalanyl}-amino-4-(3-carboxyphenoxy)-azetidin-2-one (28)

By a method similar to the method described in example 27, the title compound (28) was obtained as a white solid by reacting 3-(diphenylmethoxycarbonyl)-phenol with (3S,4S)-3-{N-(3-phenylpropionoyl)-L-phenylalanyl}-amino-4-acetoxy-azetidin-2-one following desubstitution of the diphenylmethyl group.

Yield: 8.6%; m.p.: 190° C. (dec.); Negative FAB-MS: 500 (M–H)$^-$, calcd for $C_{28}H_{27}N_3O_6$ 501; IR (KBr, cm$^{-1}$): 3410, 3285, 1770, 1650, 1560, 1380, 1230; $^1$H NMR(DMSO-d$_6$), δ (ppm): 2.37 (2H, t, J=7.7 Hz), 2.73 (2H, t, J=7.7 Hz), 2.84 (1H, dd, J=9.2 & 13.8 Hz), 3.10 (1H, dd, J=5.1 & 13.8 Hz), 4.57 (1H, m), 4.80 (1H, d, J=8.4 Hz), 5.6 (1H, d, J=5.8 Hz), 6.83 (1H, d, J=7.9 Hz), 7.2 (12H, m), 7.47 (1H, d, J=11.3), 9.4 (2H, s).

EXAMPLE 29

(3S,4S)-3-{N-(3-phenylpropionoyl)-L-phenylalanyl}-amino-4-{4-(L-2-N-benzyloxycarbonylamino-2-diphenylmethoxycarbonyl-ethyl)-phenoxy}-azetidin-2-one (29A) and (3S,4S)-3-{N-(3-phenylpropionoyl)-L-phenylalanyl}-amino-4-{4-(L-2-amino-2-carboxy-ethyl)-phenoxy}-azetidin-2-one (29B)

By a method similar to the method described in example 26, the substituted title compound (29A) was obtained as a white solid by 4-(L-2-N-benzyloxycarbonylamino-2-diphenylmethoxycarbonyl-ethyl)-phenol with (3S,4S)-3-{N-(3-phenylpropionoyl)-L-phenylalanyl}-amino-4-acetoxy-azetidin-2-one.

Yield: 28%; $^1$H NMR(DMSO-d$_6$), δ (ppm): 2.36 (2H, m), 2.55–3.10 (6H, m), 4.35 (1H, m), 4.53 (1H, m), 4.60 (1H, d, J=8), 4.95 (2H, m), 5.45 (1H, s), 6.70–6.85 (3H, m), 7.00–7.40 (27H, m), 7.90 (1H, d, J=8), 8.20 (1H, d, J=8), 8.82 (1H, d, J=8), 9.30 (1H, s).

The substituted compound, obtained above, was desubstituted as described in example 27B and the title compound (29B) was obtained as a white solid.

Yield: 38%; m.p.: 173–175° C.; FAB-MS: 545 (MH$^+$), calcd for $C_{30}H_{32}N_4O_6$ 544; IR (KBr, cm$^-$): 3405, 1771, 1649, 1507, 1226; $^1$H NMR(DMSO-d$_6$), δ (ppm): 2.38 (2H, m), 2.55–3.10 (6H, m), 3.85 (3H, br), 4.54 (1H, m), 4.64 (1H, d, J=8), 5.50 (1H, s), 6.80 (2H, d, J=8), 7.05–7.30 (12H, m), 8.38 (1H, d, J=8), 8.91 (1H, d, J=8), 9.35 (1H, s).

EXAMPLE 30

(3S,4S)-3-(N-benzyloxycarbonyl-L-phenylalanyl)-amino-4-{4-(diphenylmethoxycarbonyl)-phenoxy}-azetidin-2-one (3A) and (3S,4S)-3-(L-phenylalanyl)-amino-4-(4-carboxyphenoxy)-azetidin-2-one (30B)

BY a method similar to the method described in example 20, the substituted title compound (30A) was obtained as a white solid by reacting 4-(diphenylmethoxycarbonyl) phenol with (3S,4S)-3-(N-benzyloxycarbonyl-L-phenylalanyl)-amino-4-acetoxy-azetidin-2-one prepared from example 7.

Yield: 26%; $^1$H NMR(CDCl$_3$), δ (ppm): 3.10 (2H, m), 4.50 (2H, d, J=7.4 Hz), 5.03 (2H, m), 5.51 (1H, bs), 5.78 (1H, s), 6.84 (2H, d, J=8.8 Hz), 7.03–7.42 (23H, m), 8.08 (2H, d, J=8.8 Hz).

The protected compound (30A), obtained above, was desubstituted as described in example 27B and the title compound (30B) was obtained as a white solid.

Yield: 62%; m.p.: 180° C. (dec.); Negative FAB-MS: 468 (M–H)$^-$, calcd for $C_{19}H_{19}N_3O_5$ 469 IR (KBr, cm$^{-1}$): 3450, 1770, 1600, 1560, 1380, 1230; $^1$H NMR(CDCl$_3$), δ (ppm): 2.69 (1H, dd, J=8.9 & 13.3 Hz), 2.96 (1H, dd, J=5.1 & 13.3 Hz), 3.48 (1H, t, J=6.6 Hz), 4.66 (1H, s), 5.61 (1H, s), 6.83 (2H, d, J=8.6 Hz), 7.23 (5H, s), 7.89 (2H, d, J=8.6 Hz), 8.8 (1H, s), 9.3 (1H, s).

EXAMPLE 31

(3R,4S)-3-(N-benzyloxycarbonyl-L-phenylalanyl)-amino-4-phenylthio-azetidin-2-one-1-sulfonic acid (31)

(3S,4S)-3-(N-benzyloxycarbonyl-L-phenylalanyl)-amino-4-phenylthio-azetidin-2-one (100 mg, 0.21 mmol) obtained in example 20 in DMF (3 ml) was cooled to 0° C. and SO$_3$-DMF (49 mg, 0.32 mmol) added. The reaction mixture was stirred at room temperature for 2 hrs. After removal of DMF under vacuum, a solution of KH$_2$PO$_4$ (44 mg, 0.32 mmol) in 3 ml of water was added. After lyophilization, the solid was dissolved in water-acetonitril (1:1) and purified by reversed-phase thin-plate chromatography using water-acetonitril (2:8) as eluent. The title compound (90 mg) was obtained as a white solid after lyophilization.

Yield: 77%; m.p. 103–105° C. (dec.); Negative FAB-MS: 554 (M–H)$^-$, calcd for $C_{26}H_{25}N_3O_7S_2$ 555; IR (KBr, cm$^{-1}$): 3310, 1772, 1702, 1522, 1454, 1245; $^1$H NMR(DMSO-d$_6$), δ (ppm): 2.74 (1H, dd, J=14, 10), 3.01 (1H, dd, J=14, 4), 4.22 (1H, m), 4.51 (1H, dd, J=8, 2), 4.96 (3H, m), 7.10–7.40 (13H, m), 7.63 (2H, m), 7.52 (1H, d, J=8), 9.04 (1H, d, J=8).

EXAMPLE 32

(3S,4S)-3-(N-benzyloxycarbonyl-L-phenylalanyl)-amino-4-acetoxy-azetidin-2-one-1-sulfonic acid (32)

A solution of (3S,4S)-3-(N-benzyloxycarbonyl-L-phenylalanyl)-amino-4-acetoxy-azetidin-2-one (300 mg, 0.706 mmol) and sulfur trioxide pyridine complex (337 mg, 2.12 mmol) in anhydrous pyridine (5 ml) was refluxed for 40 mins. The mixture was cooled down and poured into $KH_2PO_4$ solution (0.5N, 50 ml). The aqueous solution was extracted with $CH_2Cl_2$ (2×25 ml) and the resulting organic phase was back-extracted with $KH_2PO_4$ solution (0.5N, 50 ml). The combined aqueous solution was treated with tetrabutylammonium hydrogen sulphate (240 mg, 0.706 mmol) and extracted with $CH_2Cl_2$ (3×30 ml). The combined organic extracts were dried over $Na_2SO_4$ and concentrated to pale yellow syrup. The crude product was subjected to flash column chromatography (silica gel, MeOH/Ethyl acetate: 1/9) to give a white solid (56 mg).

Yield: 16%; m.p.: 181° C. (dec.); Negative FAB-MS: 504 (M–H)$^-$, calcd for $C_{22}H_{23}N_3O_9S$ 505; IR (KBr, cm$^{-1}$): 3370, 1780, 1760, 1700, 1520, 1245; $^1$H NMR(CD$_3$CN/D$_2$O), δ (ppm): 2.06 (3H, s), 2.86 (1H, dd, J=9.4 & 13.8 Hz), 2.89 (1H, dd, J=5.2 & 13.8 Hz), 4.51 (1H, m), 4.55 (1H, s), 4,94 (1H, d, J=16.0 Hz), 5.06 (1H, d, J=16.0 Hz), 6.00 (1H, d, J=10.1 Hz), 6.32 (1H, s), 7.23 (10H, m), 7.66 (J=8.0 Hz).

EXAMPLE 33

(3S,4S)-3-(N-benzyloxycarbonyl-L-alanyl)-amino-4-acetoxy-azetidin-2-one (33)

By a method analogous to the method described in example 7, the title compound was obtained by reacting N-benzyloxycarbonyl-L-alanine with (3S,4S)-3-amino-4-acetoxy-azetidin-2-one.

Yield: 53%; m.p.: 161–162° C.; FAB-MS: 350 (MH$^+$), calcd for $C_{16}H_{19}N_3O_6$ 349; IR (KBr, cm$^{-1}$) 3360, 1770, 1690, 1665, 1520, 1230; $^1$H NMR(CDCl$_3$), δ (ppm): 1.36 (3H, d, J=7.0 Hz), 2.09 (3H, s), 4.32 (1H, m), 4.67 (1H, d, J=7.3 Hz), 5.05 (1H, d, J=12.3 Hz), 5.13 (1H, d, J=12.3 Hz), 5.78 (1H, d, J=7.9 Hz), 5.83 (1H, s), 7.33 (5H, s), 7.53 (1H, bs).

EXAMPLE 34

(3S,4S)-3-(N-benzyloxycarbonyl-L-phenylalanyl)-amino-4-(pyrid-4-yl) thio-azetidin-2-one (34)

By a method analogous to the method described in example 20, the title compound was obtained by reacting 4-mercaptopyridine with (3S,4S)-3-(N-benzyloxycarbonyl-L-phenylalanyl)-amino-4-acetoxy-azetidin-2-one.

Yield: 8%; $^1$H NMR(DMSO-d$_6$), δ (ppm): 2.80 (1H, m), 3.05 (1H, m), 4.30 (1H, m), 4.78 (1H, m), 4.96 (3H, m), 7.10–7.40 (12H, m), 8.90 (1H, d, J=8), 9.03 (1H, d, J=8), 9.22 (1H, s).

TESTING OF INHIBITORS FOR INHIBITION OF CATHEPDIN B, L AND PAPAIN

TEST EXAMPLE 1

In Vitro Assay Procedure for Cathepsin B

The compounds of formula I compounds were tested for inhibition of Cathepsin B. The procedure used was "A. J. Barret et al, Biochem.J. (1982), 201,189–198," with the following modifications. To a 170 μl of enzyme-buffer mixture (enzyme:r rat CathB, diluted to give appr. 10 F units/min, buffer: 56 mM Na acetate, 1.124 mM EDTA, 10 mM DTT, pH5.1) a 10 μl of inhibitor (dissolved in DMSO) was added. After 10 min of incubation at room temperature a 20 μl of 5 mM substrate (N-CBZ-Phe-Arg-AMC, dissolved in DMSO) was added to initiate reaction. Reading is followed up for 10 min at the Fluoroscan reader (excitation at 380 nm, emission at 460 nm).

A plot of percentage of inhibition vs inhibitor concentration is obtained, and IC50 is determined using a linear regression calculations (concentration of inhibitor which will give 50% inhibition). Of the compounds tested so far, the compounds of claim 1 wherein $R_2$ is hydrogen are the least active.

TEST EXAMPLE 2

Assay Procedure for Cathepsin L

To a 170 μl of enzyme-buffer mixture (enzyme: r rat CathL, diluted to give appr 15 F units/min, buffer: 58.8 mM Na citrate, 1.18 mM EDTA, 235 mM sodium chloride, 5 mM DTT, pH5.0) a 10 μl of inhibitor (dissolved in DMSO) was added. After 10 min of incubation at room temperature a 20 μl of 1 mM substrate (N-CBZ-Phe-Arg-AMC, dissolved in DMSO) was added to initiate reaction. Reading is followed up for 10 min at the Fluoroscan reader (excitation at 380 nm, emission at 460 nm).

A plot of percentage of inhibition vs inhibitor concentration is obtained, and IC50 is determined using a linear regression calculations (concentration of inhibitor which will give 50% inhibition).

TEST EXAMPLE 3

Assay Procedure for Papain

To a 170 μl of enzyme-buffer mixture (enzyme:papain, diluted to give 30 mOD/min, buffer: 0.2M potassium phosphate, 1.0 mM EDTA, 5 mML Cysteine, pH6.5) a 10 μl of inhibitor (dissolved in DMSO) was added. After 10 min of incubation at room temperature, 20 μl of 10 mM substrate (N-CBZ-Pro-Phe-Arg-pNA, dissolved in DMSO) was added to initiate reaction. Reading is followed up for 3 min at the Thermomax plate reader(absorbance at 405 nm).

A plot of percentage of inhibition vs inhibitor concentration is obtained, and IC50 is determined using a linear regression calculations (concentration of inhibitor which will give 50% inhibition).

| Exampl | Cathepsin B | Cathepsin L | Papain |
|---|---|---|---|
| E-64 | 0.005 | 0.015 | 0.0025 |
| Leupeptin | 0.013 | 0.008 | 0.012 |
| 1 | >63 | nd | >63 |
| 2 | 4.81 | nd | 15.8 |
| 3 | 52 | nd | >63 |
| 4 | 13.6 | nd | 57 |
| 5 | >25 | nd | >25 |
| 6 | >25 | nd | >25 |
| 7 | 0.47 | 0.042 | 0.275 |
| 8 | 1.46 | 0.030 | 0.731 |
| 9 | 42.29 | 2.70 | 0.228 |
| 10 | 0.47 | 0.035 | nd |
| 11 | 1.66 | 1.84 | nd |
| 12 | 7.4 | 1.58 | nd |
| 13 | 39.2 | 2.31 | nd |

Table Of IC50 Values (μM)

-continued

Table Of IC50 Values ($\mu$M)

| Exampl | Cathepsin B | Cathepsin L | Papain |
|---|---|---|---|
| 14 | 24.5 | 1.29 | nd |
| 15 | 6.33 | 2.07 | nd |
| 16 | 5.68 | 0.035 | nd |
| 17 | 5.37 | 0.0315 | nd |
| 18 | 2.12 | 0.082 | nd |
| 19 | 7.22 | 0.416 | |
| 20 | 10.5 | 0.000108 | nd |
| 21 | 7.39 | 0.000126 | nd |
| 22 | 10.9 | 0.017 | nd |
| 23 | 7.01 | 0.163 | nd |
| 24 | 6.46 | 0.091 | nd |
| 25 | 11.4 | 0.78 | nd |
| 26 | 2.19 | 0.0556 | nd |
| 27 | 21.76 | 0.038 | nd |
| 28 | 0.076 | 0.228 | nd |
| 29A | 0.59 | 0.16 | nd |
| 29B | >46 | 0.292 | 0.368 |
| 30B | >68 | 5.26 | nd |
| 31 | 8.43 | 0.067 | nd |
| 32 | 0.368 | 0.026 | nd |
| 33 | 14.31 | 35.9 | 7.03 |
| 34 | 0.33 | 0.0168 | nd | nd = not determined

We claim:

1. A 4-substituted-3-{1 or 2 amino acid residue}-azetidin-2-one compound of formula I

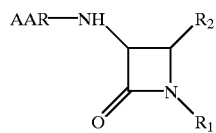

wherein
$R_1$ is selected from the group consisting of:
hydrogen;
$C_1$–$C_6$ alkyl which is unsubstituted or substituted with 1–2 substituents selected from hydroxy, halogen, cyano, carboxy and amino;
—$OR_3$ wherein $R_3$ is a $C_1$–$C_6$ alkyl which is unsubstituted or substituted by 1–2 substituents selected from hydroxy, halogen, cyano, carboxy and amino; and
—$SO_3^-M^+$ wherein M is hydrogen, a metal ion selected from the group consisting of sodium, potassium, magnesium, and calcium or $N^+(R_4)_4$ wherein $R_4$ is $C_1$–$C_6$ alkyl;
$R_2$ is selected from the group consisting of:
—$OCOR_5$ wherein $R_5$ is (i) $C_1$–$C_6$ alkyl which is unsubstituted or substituted with 1–2 substituents selected from hydroxy, halogen, cyano, heterocycle, or amino, (ii) $C_2$–$C_4$ alkenyl, (iii) $C_2$–$C_4$ alkynyl, (iv) $C_3$–$C_6$ cycloalkyl, or (v) phenyl which is unsubstituted or substituted with 1–3 substituents selected from hydroxy, halogen, $C_1$–$C_4$ alkyl, $C_1$–$C_2$ alkoxy and cyano;
—$XR_6$ wherein X is an O, S, SO, or $SO_2$ and $R_6$ is (i) $C_1$–$C_6$ alkyl which is unsubstituted or substituted with 1–2 substituents selected from hydroxy, halogen, cyano, heterocycle, or amino, (ii) $C_2$–$C_4$ alkenyl, (iii), $C_2$–$C_4$ alkynyl, (iv) $C_3$–$C_6$ cycloalkyl, (v) phenyl which is unsubstituted or substituted with 1–3 substituents selected from hydroxy, halogen, carboxy, $C_1$–$C_4$ alkyl which is unsubstituted or substituted with at least one of carboxy and amino, $C_1$–$C_2$ alkoxy or cyano, or (vi) a heterocycle;
AAR is an amino acid residue selected from the group consisting of D- and L-leucine, D- and L-isoleucine, D- and L-phenylalanine and D- and L-tyrosine, wherein the free $NH_2$ is substituted with one or more substituents selected from the group consisting of:
—$COOR_8$ wherein $R_8$ is (i) $C_1$–$C_6$ alkyl which is unsubstituted or substituted with phenyl, or (ii) phenyl; —$COR_9$ wherein $R_9$ is selected from the group consisting of (i) $C_1$–$C_6$ alkyl which is unsubstituted or substituted by 1–2 substituents selected from the group consisting of hydroxy, halogen, cyano, amino, 4-acetoxyphenyloxy, heterocycle, and phenyl, wherein the phenyl is unsubstituted or substituted by 1–2 substituents selected from halogen, hydroxy, cyano, or amino, (ii) $C_2$–$C_4$ alkenyl which is unsubstituted or substituted with heterocycle or phenyl, wherein the phenyl is unsubstituted or substituted by 1–2 substituents selected from halogen, hydroxy, cyano or amino, (iii) $C_2$–$C_4$ alkynyl, (iv) $C_3$–$C_6$ cycloalkyl, (v) a phenyl group which is unsubstituted or substituted by 1–3 substituents selected from the group consisting of hydroxy, halogen, carboxy, $C_1$–$C_4$ alkyl which is unsubstituted or substituted with at least one of carboxy, or amino or both, $C_1$–$C_2$ alkoxy group or cyano, or (vi) a heterocycle which may be mono or bicyclic; and —$SO_2R_{10}$ wherein $R_{10}$ is selected from the group consisting of (i) $C_1$–$C_6$ alkyl, (ii) $C_2$–$C_4$ alkenyl which is unsubstituted or substituted with heterocycle or phenyl, (iii) phenyl which is unsubstituted or substituted with 1–3 substituents selected from the group consisting of hydroxy, halogen, carboxy, $C_1$–$C_4$ alkyl group, $C_1$–$C_2$ alkoxy group and cyano, and (iv) naphthyl which is unsubstituted or substituted by 1–3 substituents selected from hydroxy, halogen, cyano, carboxy, $C_1$–$C_4$ alkyl, or $C_1$–$C_2$ alkoxy,
or a pharmaceutically acceptable salt of said compound of formula I.

2. A compound of claim 1 wherein said free $NH_2$ of said amino acid residue is substituted with a group selected from the group consisting of aryloxy carbonyl, alkoxy carbonyl, substituted alkanoyl, arylalkanoyl, arylalkenoyl, heterocycloalkenoyl, heterocycloalkanoyl, alkylsulphonyl, arylsulphonyl, arylalkanylsulphonyl, arylalkensulphonyl, heterocycloalkanylsulphonyl, heterocycloalkensulphonyl, and heterocyclosulphonyl.

3. A compound of claim 1 wherein the heterocycle has 1–3 heteroatoms, wherein the heteroatoms are selected from the group consisting of nitrogen, sulphur, and oxygen, as substituent for $R_5$, $R_6$, $R_9$, and $R_{10}$ are selected from the group consisting of thiophene, pyridine, 1,2,3-triazole, 1,2,4-triazole, quinoline, benzofuran, benzothiophene, morpholine, thiomorpholine, piperazine, and piperidine.

4. A compound of claim 1 wherein $R_1$ is selected from the group consisting of hydrogen, methoxy, 2-carboxy ethoxy, 2-aminoethoxy, 2-carboxy ethyl, 2-aminoethyl and sulphonic acid.

5. A compound of claim 1 wherein $R_2$ is selected from the group consisting of hydrogen, methyl, 2-amino ethyl, 2-carboxy ethyl, acetoxy, butyloxy, 3-methyl propyloxy, 1,1-dimethyl ethoxy, 2-carboxy ethyloxy, 2-aminoethyloxy, 2-fluoro ethoxy, 2-(1,2,3-triazol-4-yl)-ethoxy, cyclopentyloxy, cyclohexyloxy, cyclohexylthio, phenoxy, phenylthio, phenylsulphonyl, 4-(2-carboxy-2-amino ethyl)-phenoxy, 4-carboxy phenoxy, 3-carboxy phenoxy, 2-pyridylthio, and 4-pyridylthio.

6. A compound of claim 1 wherein said AAR is selected from the group consisting of
N-benzyloxycarbonyl phenylalanine,
N-(3-phenyl propanoyl)-phenylalanine,
N-acetyl phenylalanine,
N-{2(4-acetoxyphenoxy)-ethanoyl}-phenylalanine,
N-(morpholin-4-yl-carbonyl)-phenylalanine,
N-{3-(morpholin-4-yl)-propanoyl}-phenylalanine,
N-{3-(pyridin-3-yl)-propanoyl}-phenylalanine,
N-(benzofuran-2-yl-carbonyl)-phenylalanine,
N-{3-(thiophen-2-yl)-prop-2-enoyl}-phenylalanine,
N-{4-(1,1-dimethyl ethyl phenyl)-sulphonyl}-phenylalanine,
N-(naphthalen-2-yl-sulphonyl)-phenylalanine,
N-(3-phenyl-prop-2-en-sulphonyl)-phenylalanine,
N-benzyloxycarbonyl leucine,
N-benzyloxycarbonyl isoleucine,
N-3-phenyl propanoyl leucine, and
N-3-phenyl propanoyl isoleucine.

7. A compound of claim 1 having (3R,4S), (3R,4R), (3S,4R) or (3S,4S) configuration at the two asymmetric carbons 3 and 4 on the azetidin-2-one ring system, or a racemic mixture thereof.

8. A compound of claim 1 wherein said 1–2 amino acid residue is a D, or L isomer.

9. A compound of claim 1 wherein AAR is a 1 amino acid residue.

10. A compound of claim 1 wherein the AAR is a 2 amino acid residue.

11. A compound of claim 1 selected from the group consisting of:
(3S)-3-(N-benzyloxycarbonyl-L-phenylalanyl)-amino-1-methoxy-azetidin-2-one;
(3R)-3-(N-benzyloxycarbonyl-L-phenylalanyl)-amino-1-methoxy-azetidin-2-one;
(3S,4S)-3-(N-benzyloxycarbonyl-L-phenylalanyl)-amino-4-acetoxy-azetidin-2-one;
(3S,4S)-3-(N-benzyloxycarbonyl-L-leucyl)-amino-4-acetoxy-azetidin-2-one;
(3S,4S)-3-(N-acetyl-L-phenylalanyl)-amino-4-acetoxy-azetidin-2-one;
(3S,4S)-3-{N-(3-phenylpropionoyl)-L-phenylalanyl}-amino-4-acetoxy-azetidin-2-one;
(3S,4S)-3-{N-(trans-3-phenylpropenoyl)-L-phenylalanyl}-amino-4-acetoxy-azetidin-2-one;
(3S,4S)-3-{N-(morpholin-4-yl-carbonyl)-L-phenylalanyl}-amino-4-acetoxy-azetidin-2-one;
(3S,4S)-3-{N-(3-morpholin-4-yl-propionoyl)-L-phenylalanyl}-amino-4-acetoxy-azetidin-2-one;
(3S,4S)-3-{N-(3-pyrid-3-yl-propionoyl)-L-phenylalanyl}-amino-4-acetoxy-azetidin-2-one;
(3S,4S)-3-[N-{2-(4-acetoxyphenoxy)-ethnoyl}-L-phenylalanyl]-amino-4-acetoxy-azetidin-2-one;
(3S,4S)-3-{N-(benzofuran-2-yl-carbonyl)-L-phenylalanyl}-amino-4-acetoxy-azetidin-2-one;
(3S,4S)-3-[N-{3-(thiophen-2-yl)-trans-prop-2-enoyl}-L-phenylalanyl]-amino-4-acetoxy-azetidin-2-one;
(3S,4S)-3-[N-{4-(1,1-dimethyl ethyl phenyl)-sulfonyl)-L-phenylalanyl]-amino-4-acetoxy-azetidin-2-one;
(3S,4S)-3-{N-(naphthalen-2-yl-sulfonyl)-L-phenylalanyl}-amino-4-acetoxy-azetidin-2-one;
(3R,4S)-3-(N-benzyloxycarbonyl-L-phenylalanyl)-amino-4-phenylthio-azetidin-2-one;
(3R,4S)-3-(N-benzyloxycarbonyl-L-phenylalanyl)-amino-4-phenylsulfonyl-azetidin-2-one;
(3S,4S)-3-(N-benzyloxycarbonyl-L-phenylalanyl)-amino-4-phenoxy-azetidin-2-one;
(3S,4S)-3-(N-benzyloxycarbonyl-L-phenylalanyl)-amino-4-butyloxy-azetidin-2-one;
(3S,4S)-3-(N-benzyloxycarbonyl-L-phenylalanyl)-amino-4-(2-methyl propyloxy)-azetidin-2-one;
(3S,4S)-3-(N-benzyloxycarbonyl-L-phenylalanyl)-amino-4-(1,1-dimethylethoxy)-azetidin-2-one;
(3S,4S)-3-{N-(3-phenylpropionoyl)-L-phenylalanyl}-amino-4-phenoxy-azetidin-2-one;
(3S,4S)-3-{N-(3-phenylpropionoyl)-L-phenylalanyl}-amino-4-(4-diphenylmethoxy carbonylphenoxy)-azetidin-2-one;
(3S,4S)-3-{N-(3-phenylpropionoyl)-L-phenylalanyl}-amino-4-(4-carboxyphenoxy)-azetidin-2-one;
(3S,4S)-3-{N-(3-phenylpropionoyl)-L-phenylalanyl}-amino-4-(3-carboxyphenoxy)-azetidin-2-one;
(3S,4S)-3-{N-(3-phenylpropionoyl)-L-phenylalanyl}-amino-4-{4-(L-2-benzyloxy-carbonylamino-2-diphenylmethoxycarbonyl ethyl)-phenoxy}-azetidin-2-one;
(3S,4S)-3-{N-(3-phenylpropionoyl)-L-phenylalanyl}-amino-4-{4-(L-2-amino-2-carboxy ethyl)-phenoxy}-azetidin-2-one;
(3S,4S)-3-(N-benzyloxycarbonyl-L-phenylalanyl)-amino-4-(4-diphenylmethoxycarbonyl phenoxy)-azetidin-2-one;
(3R,4S)-3-(N-benzyloxycarbonyl-L-phenylalanyl)-amino-4-phenylthio-azetidin-2-one-1-sulfonic acid;
(3S,4S)-3-(N-benzyloxycarbonyl-L-phenylalanyl)-amino-4-acetoxy-azetidin-2-one-1-sulfonic acid and;
(3R,4S)-3-(N-benzyloxycarbonyl-L-phenylalanyl)-amino-4-(period-4-yl-thio)-azetidin-2-one.

12. A compound of claim 1, wherein AAR is N-(3-phenylpropionoyl)-phenylalanyl, $R_1$ is hydrogen and $R_2$ is 4-(2-amino-2-carboxy ethyl) phenoxy.

13. A salt as recited in claim 1, wherein said salt is the salt of an acid selected from hydrogen chloride, tartaric acid, succinic acid, fumaric acid and p-toluenesulfonic acid, or said salt contains a metal cation selected from the group consisting of sodium, potassium, magnesium and calcium.

14. A composition comprising a racemic mixture of optical isomers of a compound as recited in claim 1.

15. A pharmaceutical composition suitable for the treatment of muscular dystrophy, bone resorption, myocardial infarction or, and cancer metastasis, comprising a compound or salt as recited in claim 1 in an amount effective to inhibit cysteine proteinase, and a pharmaceutically acceptable excipient.

16. A method of inhibiting cysteine protease in a patient in need of such treatment, comprising administering to said patient a cysteine protease inhibiting effective amount of a compound or salt as recited in claim 1.

17. A method of treatment of muscular dystrophy comprising administering an effective amount of a compound or salt as recited in claim 1 to a mammal in need of such treatment.

18. A method of treatment of disturbances of bone resorption comprising administering an effective amount of a compound or salt as recited in claim 1 to a mammal in need of such treatment.

19. A method of treatment of myocardial infarction comprising administering an effective amount of a compound or salt as recited in claim 1 to a mammal in need of such treatment.

20. A method of treatment of cancer metastasis wherein the cancers are selected from the group consisting of breast, lung, liver, colon, brain, and prostate, comprising administering an effective amount of a compound or salt as recited in claim 1 to a mammal in need of such treatment.

21. A method of inhibiting cysteine proteinases in a mammal comprising administering an effective amount of a compound or salt as recited in claim 1 to a mammal in need of such treatment.

* * * * *